Figure 1:
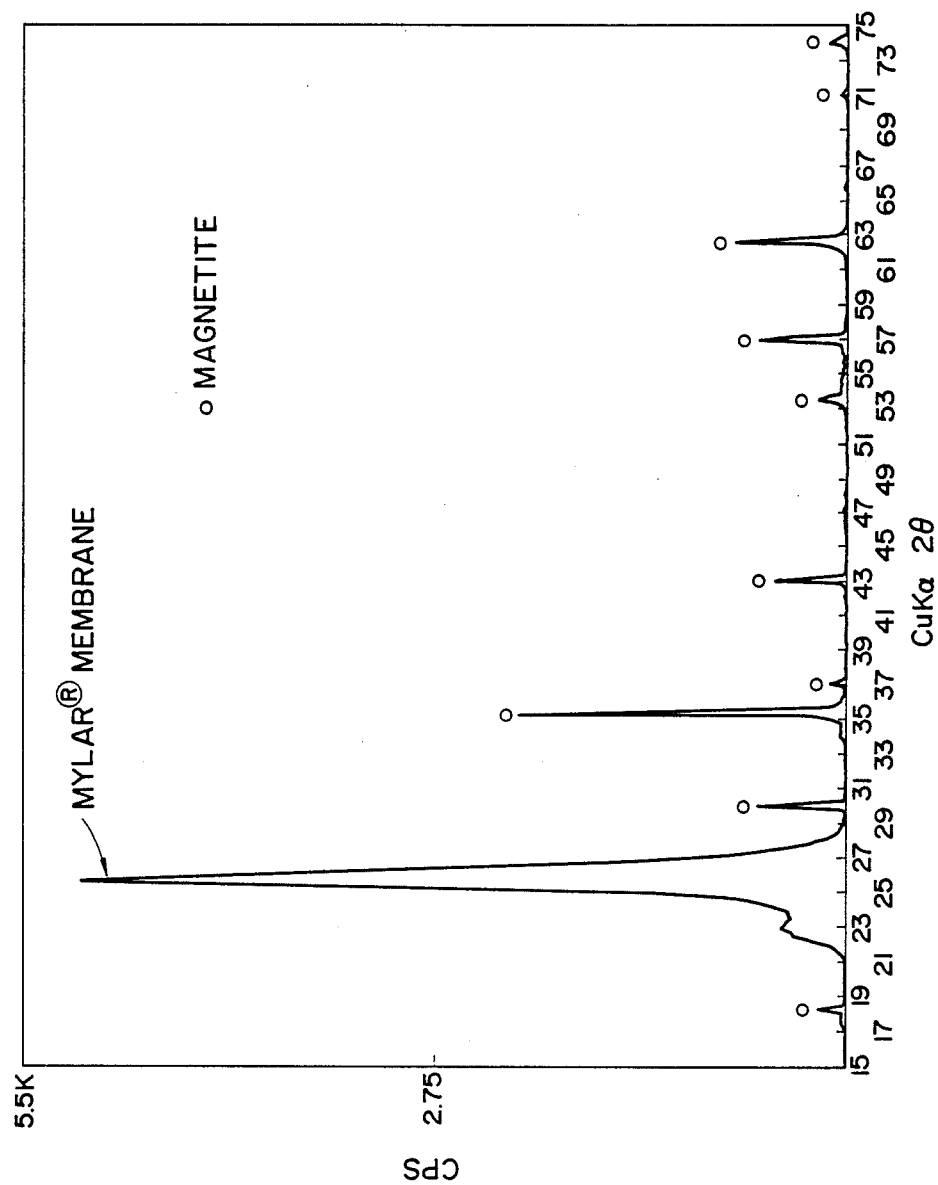

United States Patent [19]

Hamaya et al.

[11] Patent Number: 4,945,049

[45] Date of Patent: Jul. 31, 1990

[54] METHOD FOR PREPARING MAGNETIC POWDER

[75] Inventors: Toru Hamaya, 1-D, Daiichiseifuso, 5-5, Minami 1-chome, Meguro-ku, Tokyo 152; Koki Horikoshi, 39-8, Sakuradai 4-chome, Nerima-ku, Tokyo 176, both of Japan

[73] Assignees: Research Development Corporation; Toru Hamaya; Koki Horikoshi, all of Tokyo, Japan; a part interest

[21] Appl. No.: 343,263

[22] PCT Filed: Aug. 18, 1988

[86] PCT No.: PCT/JP88/00814

§ 371 Date: Apr. 14, 1989

§ 102(e) Date: Apr. 14, 1989

[87] PCT Pub. No.: WO89/01521

PCT Pub. Date: Feb. 23, 1989

[30] Foreign Application Priority Data

Aug. 18, 1987 [JP] Japan .................................. 62-204815

[51] Int. Cl.$^5$ ............................................... C12P 3/00
[52] U.S. Cl. ..................................................... 435/168
[58] Field of Search ........................................... 435/168

[56] References Cited

U.S. PATENT DOCUMENTS

| 4,385,119 | 5/1983 | Blakemore et al. | 435/168 |
| 4,394,451 | 2/1983 | Blakemore et al. | 435/168 |

FOREIGN PATENT DOCUMENTS

| 0684552 | 4/1964 | Canada | 435/168 |
| 0744701 | 10/1966 | Canada | 435/168 |
| 0187192 | 11/1983 | Japan | 435/168 |
| 60-172288 | 9/1985 | Japan . | |
| 2055092 | 3/1987 | Japan | 435/168 |
| 62-171688 | 7/1987 | Japan . | |
| 62-294089 | 12/1987 | Japan . | |
| 2192870 | 4/1988 | United Kingdom | 435/168 |

*Primary Examiner*—Herbert J. Lilling
*Attorney, Agent, or Firm*—Oblon, Spivak, McClelland, Maier & Neustadt

[57] ABSTRACT

The present invention relates to a method for preparing magnetic powder comprising homogeneous and fine particles using an alkali-producing enzyme. The object of the present invention is to provide a method suitable for preparing magnetic powder comprising relatively small particles, for instance, fine particles having a particle size ranging from 50 to 500 nm. The present invention relates to a method for preparing at least one member selected from the group consisting of iron oxides, iron hydroxides and iron oxyhydroxides which comprises the step of alkalizing a solution containing iron ions utilizing an alkali-producing enzyme and a substrate of the enzyme.

According to the present invention, there can be produced magnetite ($Fe_3O_4$) and maghemite (gamma-$Fe_2O_3$) useful as magnetic powder as well as goethite (alpha-FeO(OH)), hematite (alpha-$Fe_2O_3$) and lepidocrocite (gamma-FeO(OH)) useful as the starting materials thereof. The magnetic powder can be used as the materials for magnetic recording and magnetic fluid; carriers for bioreactors; those for magnetic separation of cells and biopolymers; and those for microcarriers of medicines.

16 Claims, 7 Drawing Sheets

(×10,000)

1μm

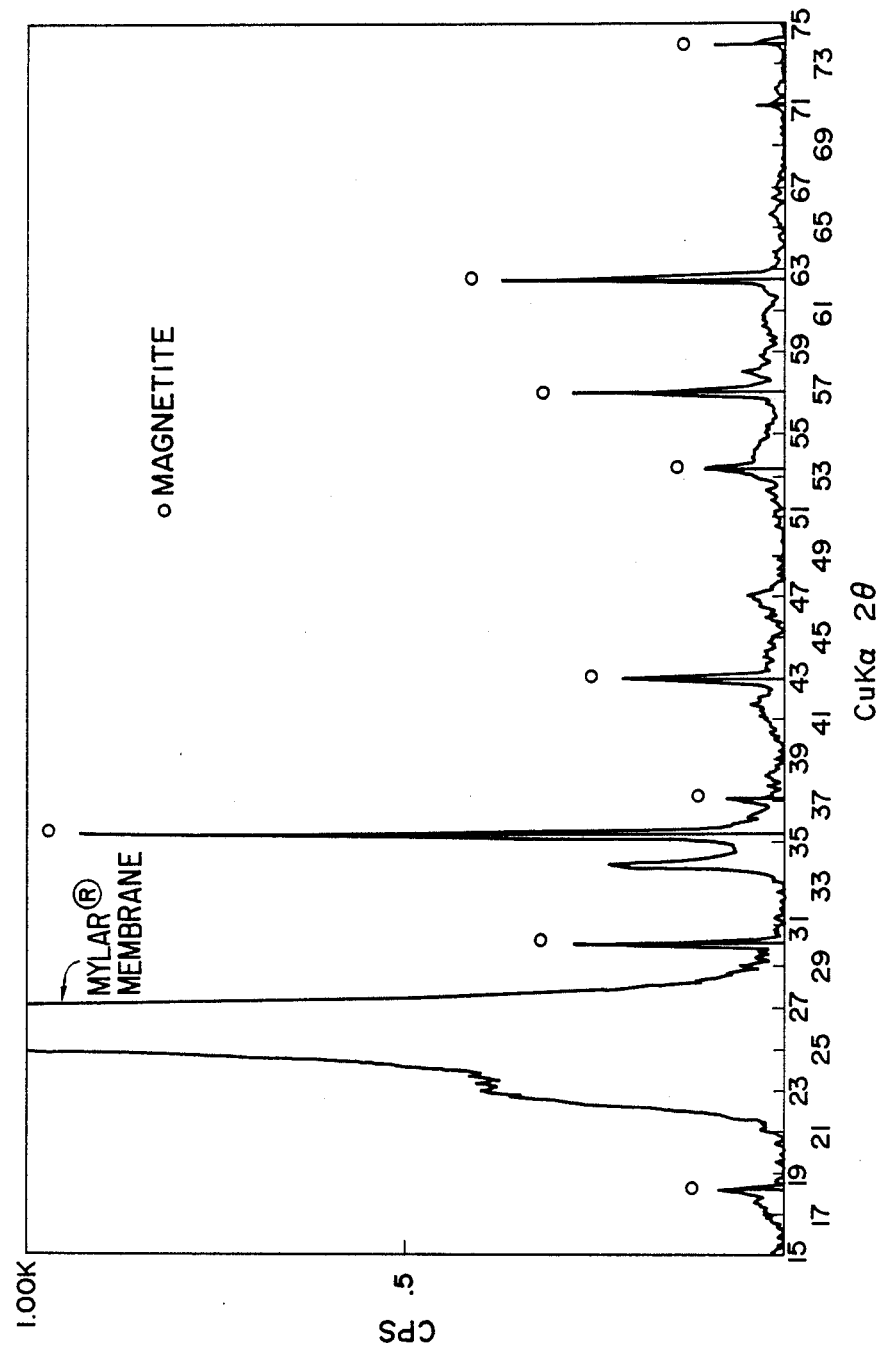

METHOD FOR PREPARING MAGNETIC POWDER

FIELD OF THE INVENTION

The present invention relates to a method for preparing magnetic powder and more particularly to a method for preparing uniform fine particles of magnetic powder utilizing an alkali-producing enzyme.

BACKGROUND OF THE INVENTION

A method which comprises adding a precipitant to a metal salt solution to form precipitates of a metal hydroxide has been used to prepare magnetic powder. However, when the precipitant is externary added to such a solution, the concentration of the precipitant in the solution becomes instantaneously and locally high and the resultant precipitates are likely to cause impurities uptake even if the concentration of the precipitant is low and it is added in small portions with stirring. On the contrary, use of a homogeneous precipitation method makes it possible to provide pure and compact precipitates. This homogeneous precipitation method is a method in which a precipitant is gradually produced in the solution by a chemical reaction such as hydrolysis. According to this method, the concentration of the precipitant is always maintained at an extremely low level since the produced precipitant is immediately consumed. As a result, the incorporation of impurities into the resultant precipitates and the amount of bound water are maintained at a low level because the precipitated particles slowly grow with time and precipitates of small volume is prepared.

Among the homogeneous precipitation methods, the most frequently used is an urea method in which a metal hydroxide or oxide is prepared utilizing a hydrolysis reaction of urea. The urea method is used to prepare a hydroxide or an oxide of iron.

However, it is found that the particle size of powder of such an oxide or the like prepared by the homogeneous precipitation method is large. Accordingly, an object of the present invention is to provide a method which is suitable to prepare magnetic powder consisting of a relatively small particles such as fine particles having an average particle size ranging from about 50 to 500 nm.

DISCLOSURE OF THE INVENTION

The present invention relates to a method for preparing at least one member selected from the group consisting of iron oxides, iron hydroxides and iron oxyhydroxides, which comprises a step of alkalizing a solution containing iron ions using an alkali-producing enzyme and a substrate thereof.

BRIEF EXPLANATION OF THE ACCOMPANYING DRAWINGS

Figure 2:
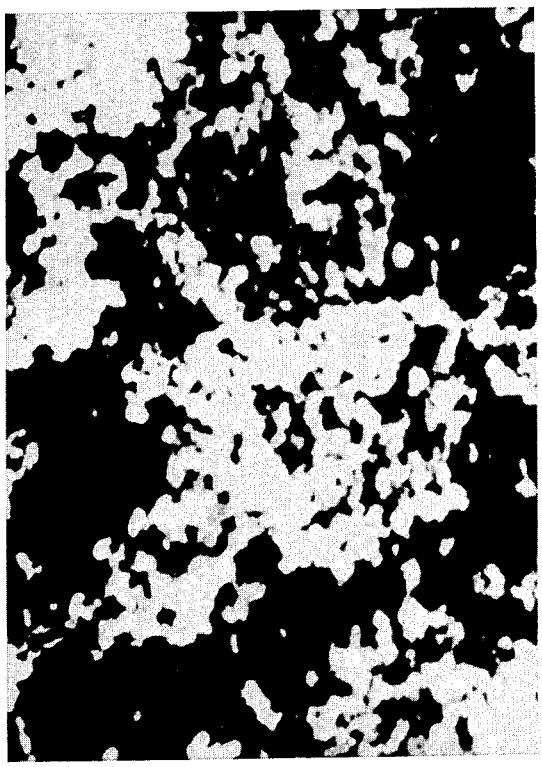

FIGS. 1 and 3 to 7 are X-ray diffraction patterns and FIG. 2 is a photograph illustrating the particle structure of the product obtained in Example 1.

MOST PREFERRED EMBODIMENTS FOR CARRYING OUT THE INVENTION

The present invention will now be explained in detail.

In the method of the present invention, a solution containing iron ions is used. The solution contains either ferric or ferrous ions or both of these. The sources of these ferric and ferrous ions are not restricted to specific ones and specific examples thereof include chlorides, sulfates, nitrates, lactates, oxalates, fumalates, ammonium sulfates and ammonium oxalates of iron (including both ferric and ferrous salts).

In the method of the present invention, the aforementioned solution containing iron ions is alkalized with an alkali-producing enzyme and a substrate thereof.

The term "alkali-producing enzyme(s)" used herein means an enzyme capable of forming an alkali substance through a reaction with the substrate thereof and, for instance, hydrolases and oxidoreductases can be used. Further, the invention encompasses a method in which the solution containing iron ions is alkalized using a bacterial cell capable of producing an alkali-producing enzyme. Examples of hydrolases and substrates thereof which can be used in the invention are listed in Table I and oxidoreductases and substrates thereof are shown in Table II. In addition, bacteria which produce urease serving as an alkali-producing enzyme are exemplified in Table III and examples of other bacteria capable of producing an alkali-producing enzyme are shown in Table IV.

TABLE I

| Hydrolases and Substrates Thereof | | |
|---|---|---|
| Enzyme No. | Name of Enzyme | Substrate |
| 3.5.1.1 | asparaginase | L-asparagine |
| 3.5.1.2 | glutaminase | L-glutamine |
| 3.5.1.3 | omega-amidase | omega-amidodicarboxylate |
| 3.5.1.4 | amidase | monocarboxylate |
| 3.5.1.5 | urease | urea |
| 3.5.1.6 | beta-ureidopropionase | N-carbamoyl-beta-alanine |
| 3.5.1.7 | ureidosuccinase | N-carbamoyl-L-alanine |
| 3.5.1.12 | biotinidase | biotinamide |
| 3.5.1.19 | nicotinamidase | nicotinamide |
| 3.5.1.20 | citrullinase | L-citrulline |
| 3.5.1.29 | alpha-(acetamidomethylene)-succinate hydrolase | alpha-(acetamidomethylene)-succinate |
| 3.5.1.30 | 5-aminovaleramidase | 5-amino-n-valeramide |
| 3.5.1.35 | D-glutaminase | D-glutamine |
| 3.5.1.38 | glutaminase (asparaginase) | L-glutamine/L-asparagine |
| 3.5.1.43 | peptidyl-glutaminase | alpha-N-peptidyl-L-glutamine |
| 3.5.1.44 | glutaminyl-peptide glutaminase | L-glutaminyl-peptide |
| 3.5.1.45 | urease (ATP-hydrolyzing) | urea |
| 3.5.3.5 | formiminoaspartate deiminase | N-formimino-L-aspartate |
| 3.5.3.6 | arginine deiminase | L-arginine |
| 3.5.3.9 | allantoate deiminase | allantoate |
| 3.5.3.12 | agmatine deiminase | agmatine |
| 3.5.3.13 | formiminoglutamate deiminase | N-formimino-L-glutamate |
| 3.5.4.1 | cytosine deaminase | cytosine |
| 3.5.4.2 | adenine deaminase | adenine |
| 3.5.4.3 | guanine deaminase | guanine |
| 3.5.4.4 | adenosine deaminase | adenosine |
| 3.5.4.5 | cytidine deaminase | cytidine |
| 3.5.4.6 | AMP deaminase | AMP |
| 3.5.4.7 | ADP deaminase | ADP |
| 3.5.4.8 | aminoimidazolase | 4-aminoimidazole |
| 3.5.4.11 | pterin deaminase | pterin |
| 3.5.4.12 | dCMP deaminase | dCMP |
| 3.5.4.13 | dCTP deaminase | dCTP |
| 3.5.4.14 | deoxycytidine deaminase | deoxycytidine |
| 3.5.4.15 | guanosine deaminase | guanosine |
| 3.5.4.17 | adenosine phosphoric acid deaminase | AMP |
| 3.5.4.18 | ATP deaminase | ATP |
| 3.5.4.20 | pyrithiamin deaminase | pyrithiamine |
| 3.5.4.21 | creatinine deiminase | creatinine |
| 3.5.4.22 | 1-pyrroline-4-hydroxy-2- | HPC |

TABLE I-continued

Hydrolases and Substrates Thereof

| Enzyme No. | Name of Enzyme | Substrate |
|---|---|---|
| | carboxylate deaminase | |
| 3.5.4.23 | blasticidin-S deiminase | blasticidine-S |
| 3.5.4.24 | cepiapterin deaminase | cepiapterin |
| 3.5.5.1 | nitrilase | 3-indole-acetonitrile |
| 3.5.5.2 | ricinine nitrilase | ricinine |
| 3.5.5.3 | cyanate hydrolase | cyanate |

TABLE II

Oxidoreductase and Substrates Thereof

| Enzyme No. | Name of Enzyme | Substrate |
|---|---|---|
| 1.6.6.4 | nitrite reductase (NAD(P)H) | nitrite |
| 1.6.6.9 | trimethylamine-N-oxidoreductase | trimethylamine-N-oxide |
| 1.6.6.11 | hydroxylamine reductase (NADH) | hydroxylamine |
| 1.7.7.1 | ferredoxin-nitrite reductase | nitrite |
| 1.7.99.1 | hydroxylamine reductase | hydroxylamine |
| 1.18.2.1 | nitrogenase | $N_2$ |
| 1.19.2.1 | nitrogenase (flavodoxin) | $N_2$ |

TABLE III

Urease (EC 3.5.1.5)-producing Bacteria

Proteus vulgaris (ATCC 13315)  Proteus columbiensis
Proteus morganii (ATCC 25830)  Micrococcus
Aerobacter aerogenes
Klebsiella pneumoniae (ATCC 13883)
Pseudomonas aeruginosa (ATCC 10145)
Escherichia coli (ATCC 11775)
Alcaligenes faecalis (ATCC 8750)  Salmonella
Vibrio cholerae (ATCC 14035)  Vibrio El Tor
Shigella  Eberthella  Enterococcus
Pneumococcus  Neisseria
Streptococcus pyogenes (ATCC 21060)
Lactobacillus acidophilus (ATCC 11506)
Lactobacillus bulgaricus (ATCC 11842)
Lactobacillus doderlenii
Brucella melitensis (ATCC 23456)
Brucella abortis (ATCC 23448)  Pasteurella pestis
Bacillus subtilis (ATCC 6633)
Mycobacterium tuberculosis (ATCC 25618)

TABLE IV

Asparaginase (EC 3.5.1.1)-producing Bacteria

Escherichia coli (ATCC 11775)
Erwinia carotovora (ATCC 25206)
Bacillus coagulans (ATCC 12245)
Fusarium tricinctum (ATCC 24631)
Proteus vulgaris (ATCC 13315)
Saccharomyces cerevisiae (ATCC 26923)

Glutaminase (EC 3.5.1.2)-producing Bacteria

Pseudomonas aeruginosa (ATCC 27107)
Escherichia coli (ATCC 11775)  yeast  Actinomyces

Adenine Diaminase (EC 3.5.4.2)-producing Bacteria

Azotobacter vinelandii (ATCC 25308)
Candida utilis (ATCC 9950)
Crithidia fasticulata (protozoan)

Guanine Deaminase (EC 3.5.4.3)-producing Bacteria

Clostridium  Pseudomonas

Adenosine Deaminase (EC 3.5.4.4)-producing Bacteria

Pseudomonas

AMP Deaminase (EC 3.5.4.6)-producing Bacteria yeast

According to the present invention, at least one member selected from the group consisting of iron oxides, iron hydroxides and iron oxyhydroxides can be prepared by alkalizing a solution containing iron ions utilizing an alkali-producing enzyme and a substrate thereof.

Products obtained by alkalization vary depending on the reaction conditions. The reaction conditions herein mean the kind of iron ions (whether they are $Fe^{2+}$ or $Fe^{3+}$), ratio (molar ratio) of the concentration of $Fe^{2+}$ to that of $Fe^{3+}$, the amount of enzymes and substrates thereof used, the state of the reaction system (whether it is oxidation or reduction system), temperature and the like.

More specifically, the method of the present invention makes it possible to prepare powder such as $Fe_3O_4$ (magnetite), alpha-FeO(OH) (goethite), beta-FeO(OH) (akaganeite), gamma-FeO(OH) (lepidocrocite), delta-FeO(OH), alpha-$Fe_2O_3$ (hematite), gamma-$Fe_2O_3$ (maghemite), Fe(OH)$_2$ and Fe(OH)$_3$.

(a) Cases Where the Solution Containing Iron Ions Contains $Fe^{2+}$ as Iron Ions:

In such a case, the alkalization of the foregoing solution results in the formation of Fe(OH)$_2$. In this connection, Fe(OH)$_2$ is relatively unstable. Therefore, in the present invention, the akalization is carried out in the presence of an oxidizing agent or an oxidizing agent is added to the reaction system after the alkalization to completely or partially oxidize $Fe^{2+}$ to $Fe^{3+}$ and magnetite or an iron oxyhydroxide are obtained. Products obtained by such an oxidation vary depending on the conditions thereof such as the oxidation temperature, molar ratio of iron ions to the substrate present in the solution, the degree of progress of the reaction and Fe$_3$O$_4$, a mixture of Fe$_3$O$_4$ and alpha-FeO(OH), alpha-FeO(OH) or a mixture of alpha-FeO(OH) and gamma-FeO(OH) can be prepared. The relation between the oxidation conditions of Fe(OH)$_2$ and the kinds of the products is disclosed in FIG. 1 attached to 1st to 25th reports on Water-containing Iron Oxides, Toshio TAKADA & Masao KIYAMA, Collected Summary for Lectures on Powder and Powder Metallurgy and in the method of the present invention, the kind of the product can be selected on the basis of the data plotted on the figure.

For instance, if the reaction temperature ranges from about 10° to 30° C., the oxidation products of Fe(OH)$_2$ are magnetite and alpha-FeO(OH) for a molar ratio of $Fe^{2+}$ to OH$^-$ of 1: about 2; alpha-FeO(OH) for the molar ratio of 1: about 3 or less; and a mixture of alpha-FeO(OH) and gamma-FeO(OH) for the molar ratio of 1: about 1.5 or less. Moreover, when the reaction temperature is not less than 50° C., magnetite is obtained at a molar ratio of $Fe^{2+}$ to OH$^-$ of 1: about 1 or more.

The oxidizing agent for oxidizing $Fe^{2+}$ is not restricted to specific ones and examples thereof include oxygen, ozone, manganese dioxide, lead dioxide, permanganates, chlorates, hydrogen peroxide, sodium peroxide, ferric salts and nitrates (sodium and potassium salts).

The resulting alpha-FeO(OH) and gamma-FeO(OH) can be converted to hematite (alpha-Fe$_2$O$_3$) and maghemite (gamma-Fe$_2$O$_3$) respectively by dehydrating them according in an ordinary method.

(b) Cases Where the Solution Containing Iron Ions Contains $Fe^{2+}$ and $Fe^{3+}$ as Iron Ions:

When the solution containing iron ions contains $Fe^{2+}$ and $Fe^{3+}$ as iron ions, magnetite can be obtained by adjusting the molar ratio of $Fe^{2+}$ to $Fe^{3+}$ to the range within which magnetite is formed, before the completion of alkalization or the end of the formation of magnetite. Magnetite can be formed at a molar ratio of $Fe^{2+}$ to $Fe^{3+}$ ranging, for instance, from 1: about 0.5 to 5, preferably 1: about 1 to 3.

When $Fe^{2+}$ is present in excess compared with the foregoing range, the molar ratio of $Fe^{2+}$ to $Fe^{3+}$ can be adjusted by carrying out the alkalization in the presence of an oxidizing agent or adding an oxidizing agent to the reaction system before the complete formation of magnetite. On the contrary, when $Fe^{3+}$ is present in excess compared with the foregoing range, the molar ratio of $Fe^{2+}$ to $Fe^{3+}$ can be controlled by carrying out the alkalization in the presence of a reducing agent or adding a reducing agent to the reaction system before the complete formation of magnetite.

The oxidizing agents used to adjust the molar ratio, $Fe^{2+}/Fe^{3+}$, are not restricted to specific ones and examples thereof are those mentioned above in connection with item (a). In addition, the reducing agents are not restricted to specific compounds either and include, for instance, hydrogen, ferrous salts and titanium ($Ti^{2+}$, $Ti^{3+}$) in low oxidized states.

Upon alkalizing the solution containing $Fe^{2+}$ and $Fe^{3+}$ in the procedures described above, iron hydroxide is first formed and the molar ratio, $Fe^{2+}/Fe^{3+}$, is adjusted if necessary, the iron hydroxide forms precipitates (hydrophobic colloid). From the hydrophobic colloid, coagulation occurs on standing and as a result the crystals of magnetite is formed. This processes are as follows:

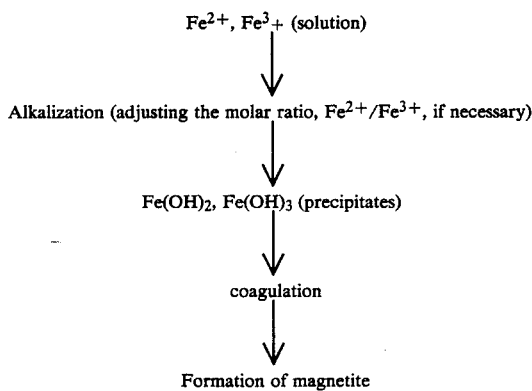

The term "magnetite" herein means not only those represented by the chemical formula: $Fe_3O_4$ but also iron oxides which contain ferric and ferrous irons and exhibit magnetic properties.

Moreover, when the solution contains $Fe^{2+}$ and $Fe^{3+}$ as iron ions and the molar ratio, $Fe^{2+}/Fe^{3+}$, is outside the range within which the magnetite is formed, for instance, $Fe(OH)_2$ is principally produced in the case where $Fe^{2+}$ is present in excess and $Fe(OH)_2$ is converted to magnetite or the like depending on the conditions as already mentioned above in connection with item (a). When $Fe^{3+}$ is present in excess, $Fe(OH)_3$ is mainly produced as will be explained in item (c) given below and $Fe(OH)_2$ derived from $Fe^{2+}$ is sometimes converted to magnetite as in item (a) depending on the concentration of $Fe^{2+}$.

(c) Cases Where the Solution Containing Iron Ions Contains $Fe^{3+}$ as Iron Ions In such a case, $Fe(OH)_3$ is produced as the product of the alkalization reaction. $Fe(OH)_3$ can be reduced according in an ordinary manner to obtain magnetite. The reducing agents used herein are not restricted to specific ones, but those described above in item (b) can be used. As to the degree of reduction, it is preferable to limit the molar ratio, $Fe^{2+}/Fe^{3+}$, to, for instance, 1: about 0.5 to 5, preferably 1: about 1 to 3, within which magnetite can be obtained.

Magnetite may also be obtained by carrying out the alkalization in the presence of a reducing agent.

The conditions of the alkalization in the method of the present invention will hereunder be explained.

In the present invention, the alkalization is initiated by adding, to a solution containing iron ions, an alkali-producing enzyme or bacteria capable of producing an alkali-producing enzyme and a substrate of the enzyme. The alkalization is preferably performed in the vicinity of the optimum conditions of the alkali-producing enzyme and the optimum conditions vary depending on the kind of the enzyme used. For instance, when urease derived from jack bean is used as such an alkali-producing enzyme, the alkalization is desirably carried out at a temperature ranging from about 10° to 60° C., preferably about 25° to 50° C.; and an initial pH of 4.5 to 6.7, preferably 6.0 to 6.7. When asparaginase is used as such an alkali-producing enzyme, the temperature ranges from 10° to 45° C., preferably 35° to 40° C.; and the initial pH of the alkalization ranges from 6.0 to 6.7. In this connection, it should be noted that the initial pH value of the alkalization be in the range within which the iron ions are not converted to hydroxides but are in the dissolved state, in other word in the neutral or acidic range.

The time required for the alkalization depends on the concentrations of iron ions, enzymes and substrates used; as well as the temperature of the reaction and the scale thereof, but it normally ranges from one hour to 5 days. In addition, the concentration of iron ions and the amount of the substrate and enzyme can be properly selected in the present invention. The concentration of iron ions in the solution is, for instance, in the range of from 0.5 to 50 mmole/l, preferably 3 to 10 mmole/l. The amount of the enzyme used is not less than 0.1 unit/ml, preferably not less than 10 unit/ml, while the amount of the substrate used is suitably 0.01 to 100 times, preferably 0.1 to 10 times the molar number of iron ions.

The alkalization reaction can be carried out in either a batchwise or continuous manner. Moreover, it is also possible to use an alkali-producing enzyme or bacteria capable of producing alkali-producing enzyme which are immobilized according in an ordinary manner.

Magnetite or the like obtained according to the method of the present invention is isolated from the solution and can be used as such after water washing or can be used as magnetic powder or a starting material therefor after subjecting it to a stabilization treatment(s). Examples of such stabilization techniques include (i) a method which comprises forming a thin oxide film on the particle surface (see Japanese Patent Un-examined Publication (hereinafter referred to as "J.P. KOKAI") No. 49-97738); (ii) a method which comprises forming a film of a higher fatty acid on the particle surface (see J.P. KOKAI No. 49-97738); (iii) a method which comprises adhering an amino-modified silicone oil or the like to the particle surface (see J.P. KOKAI No. 54-77270); and (iv) a method which comprises adhering a boron trialkoxide to the particle surface.

According to the present invention, there can be produced magnetite ($Fe_3O_4$) and maghemite (gamma- Fe$_2$O$_3$) useful as magnetic powder as well as goethite (alpha-FeO(OH)), hematite (alpha-Fe$_2$O$_3$) and lepidocrocite (gamma-FeO(OH)) useful as the starting materials for such magnetic powder. These magnetic powder can be useful as the materials for magnetic recording or magnetic fluid; carriers for bioreactors; those for magnetic separation of cells or biopolymers; those for microcarriers for medicines or the like.

The method of the present invention belongs to the homogeneous precipitation method and, therefore, this method makes it possible to obtain pure and compact precipitates and thus makes it possible to obtain fine magnetic powder. By varying the alkali-producing conditions of the enzyme used, the particle size of the resulting powder can be changed within the range of 50 to 500 nm and the particles can be formed into various shapes such as needle, spherical or polygonal prismatic forms.

In addition, the reaction equipments are heavily consumed in recent wet methods because of the use of an alkali such as sodium hydroxide or ammonia. However, the alkalization reaction is carried out in the vicinity of neutral pH utilizing an enzyme or bacteria and, therefore, such a problem does not occur in the method of the present invention.

The present invention will hereunder be explained in more detail with reference to the following Examples.

EXAMPLE 1

100 ml of an aqueous solution including 8.9 mM of urea, 4.2 mM of ferrous chloride and 0.2 M of potassium nitrate was charged into a container and was degassed with nitrogen gas. The container was sealed with a butyl rubber plug and then was maintained at 25° C. To the solution there was added 1 ml (1,000 units/ml) of an urease solution with a syringe and the solution was again maintained at 25° C. After 48 hours, black precipitates were deposited on the bottom of the container. All the precipitates exhibited magnetic susceptibility. The precipitates were examined by X-ray diffraction analysis and the results obtained were shown in FIG. 1. In addition, the electron micrograph thereof is shown in FIG. 2. These results indicate that the black precipitates are homogeneous fine particles of magnetite having a diameter of 200 nm.

EXAMPLE 2

Figure 3:
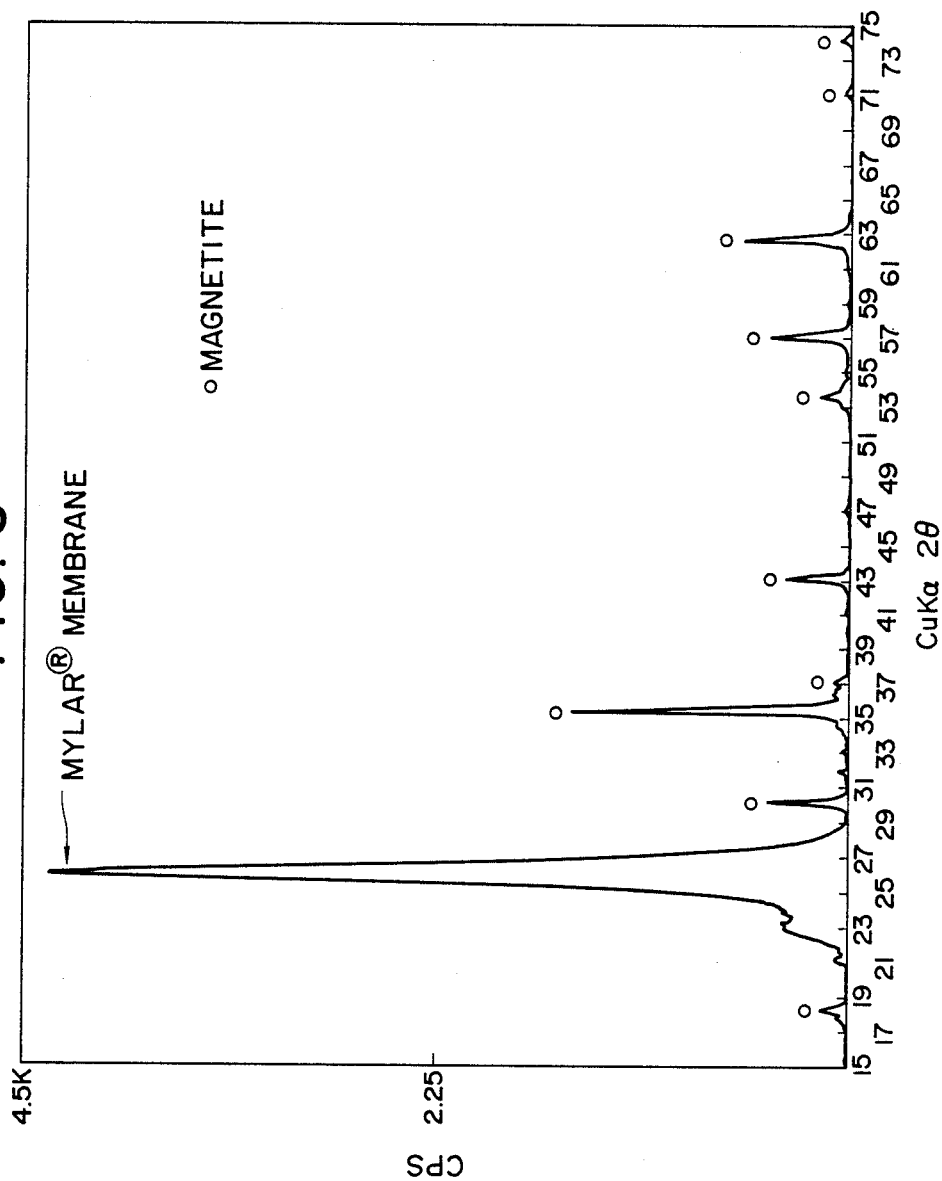

Using 100 ml of an aqueous solution containing 3.0 mM of urea, 1.4 mM of ferrous chloride and 0.2 M of potassium nitrate, the reaction was carried out as in Example 1 and as a result magnetite was obtained as in Example 1. The X-ray diffraction pattern thereof is shown in FIG. 3.

EXAMPLE 3

Figure 4:
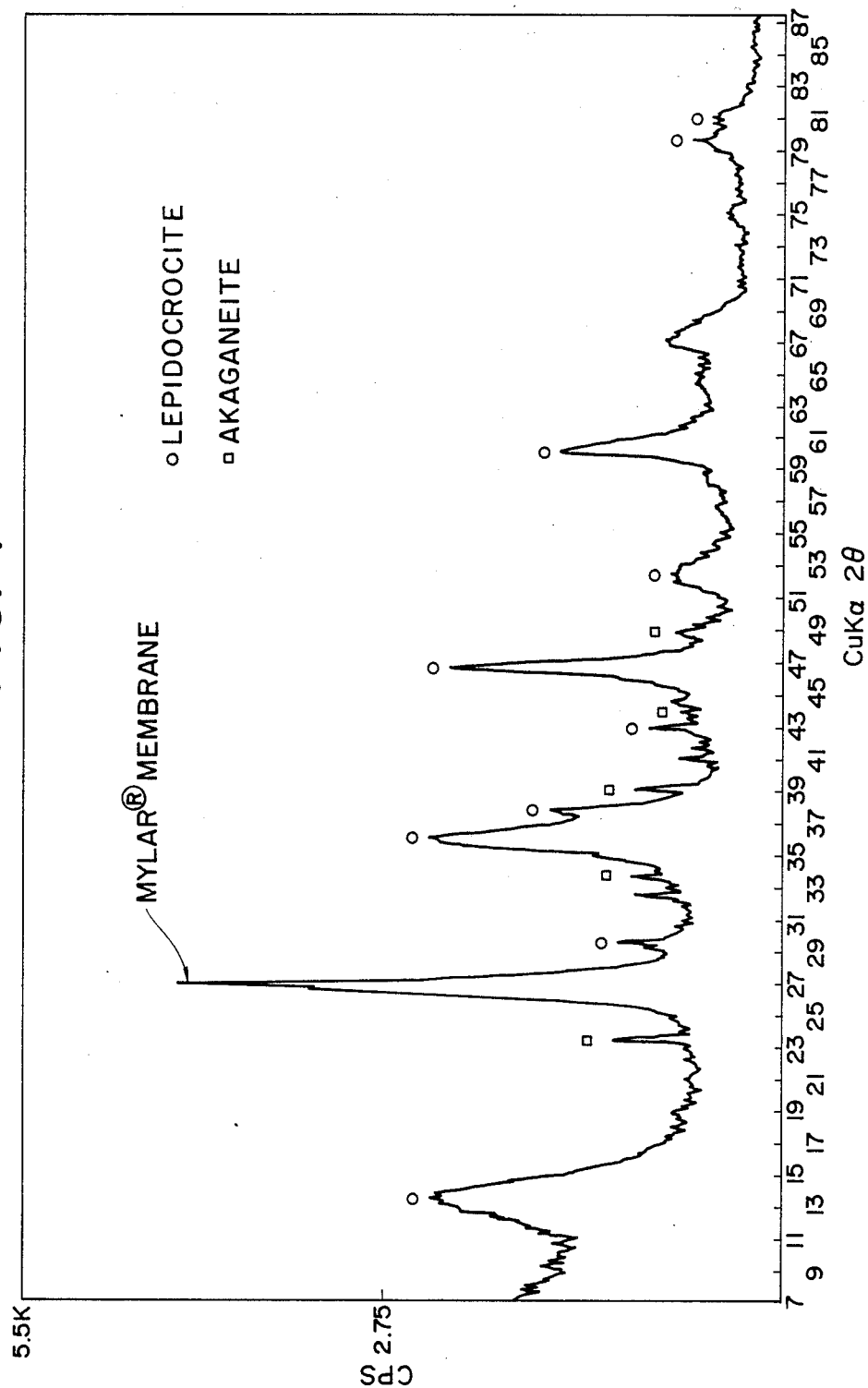

The same starting materials as those used in Example 1 were employed and air was passed through the solution in place of degassing the same with nitrogen gas. As a result, a mixture of lepidocrocite and akaganeite was produced. The X-ray diffraction pattern is shown in FIG. 4.

EXAMPLE 4

Figure 5:
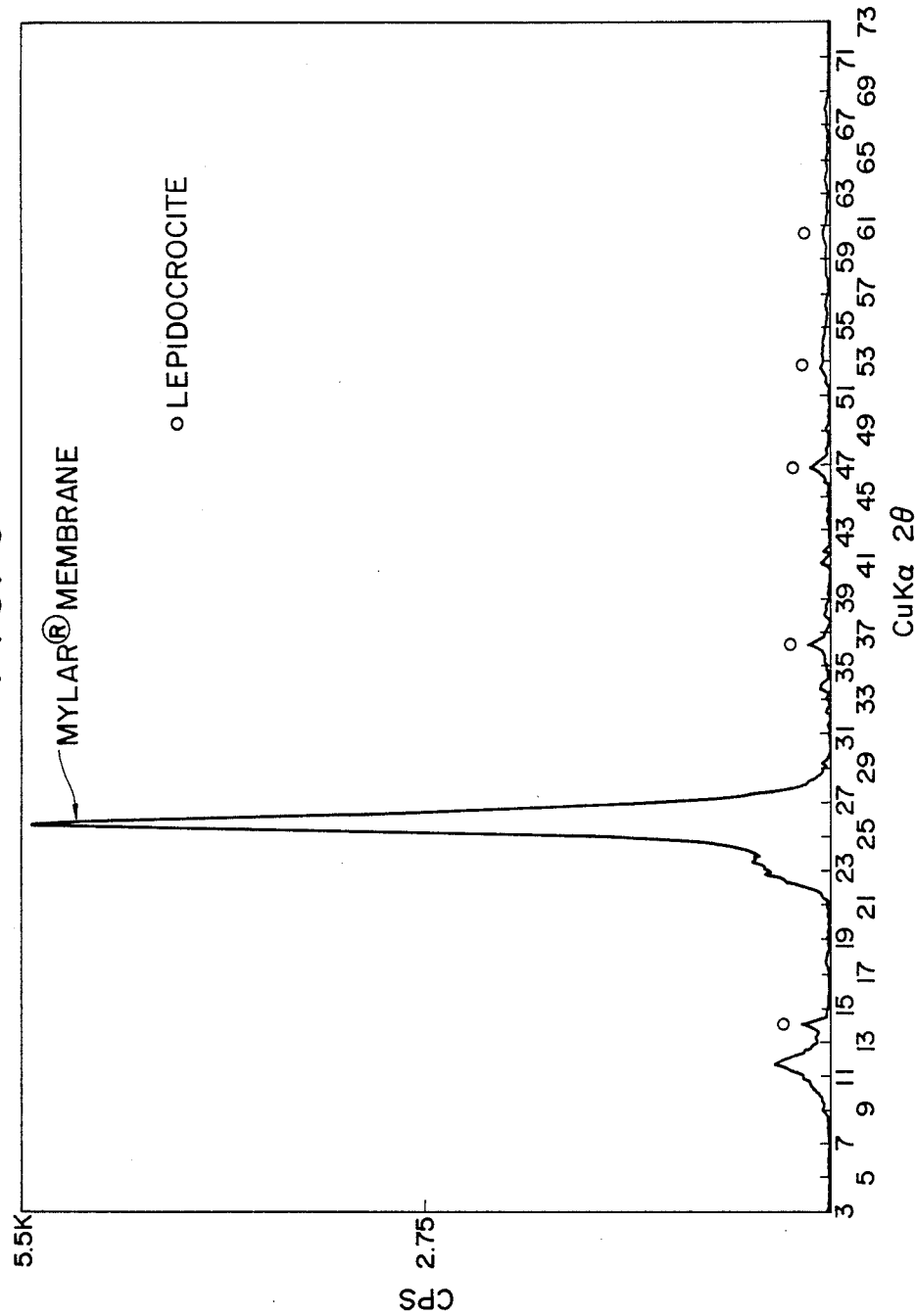
Figure 6:
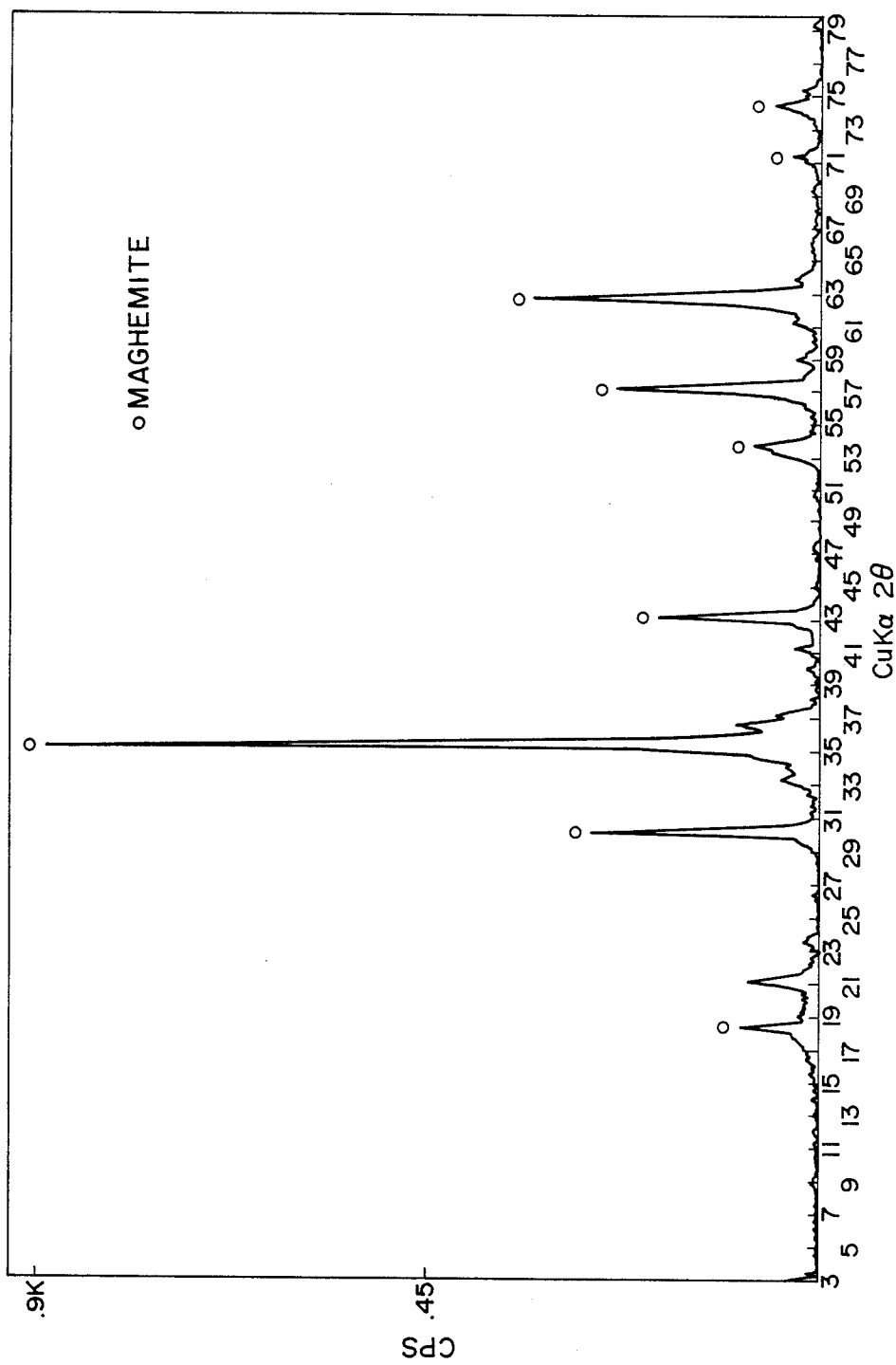

Using an aqueous solution containing 2.0 mM of urea, 4.2 mM of ferrous chloride and 0.2 M of potassium nitrate, the reaction was carried out as in Example 1 and as a result, lepidocrocite was obtained. The X-ray diffraction pattern thereof is shown in FIG. 5.

EXAMPLE 5

To 200 mg of an aqueous solution containing 200 mM of urea, 100 mg of ferrous chloride hydrate (FeCl$_2$-nH$_2$O) and 0.1 M of potassium nitrate there was added 1 ml of urease solution (1,000 units/ml), then liquid paraffin was added thereto to form a liquid paraffin layer with the thickness of about 1 cm on the surface of the solution and the solution was kept to stand at 25° C. After 48 hours, precipitates of blackish brown were deposited on the bottom of the container. The precipitates were examined by X-ray diffraction analysis (see FIG. 6) and were found to be maghemite.

EXAMPLE 6

Starting materials were dissolved into 10 ml of sufficiently degassed water to form a starting solution having concentration of 80 mM of urea, 5.0 mM of ferrous chloride and 2.0 mM of ferric chloride. The gas phase and oxygen dissolved in the solution were removed and 1 ml of an urease solution (1,000 units/ml) was added thereto during it being allowed to stand in air. After 24 hours, magnetically susceptible black precipitates were formed. It was found that the precipitates were magnetite as estimated from the color and the magnetic susceptibility.

EXAMPLE 7

The reaction was carried out as in Example 6 except that urea was used in a concentration of 8.0 mM and ferric chloride in a concentration of 2.4 mM. After 5 minutes, yellow gel-like colloid was obtained. To the colloid ferrous chloride was added to make a concentration thereof 2.4 mM. After 24 hours, magnetically susceptible black precipitates were formed. The precipitates were magnetite as in Example 6.

EXAMPLE 8

Asparaginase (0.1 ml; 1,000 units/ml) was added to a solution containing 10 mM of asparagine and 5 mM of ferrous chloride. The solution was maintained at 37° C. and two hours thereafter, the solution was centrifuged in a centrifugal separator. As a result, yellow precipitates were obtained on the bottom of a centrifugal tube, but these were not magnetically susceptible. It was found that the precipitates were lepidocrocite as estimated from the color and the pH value (6.7) after the reaction.

EXAMPLE 9

The gas phase present in 100 ml of an aqueous solution containing 8.9 mM of urea, 4.2 mM of ferrous chloride and 0.2 M of potassium nitrate was replaced with nitrogen gas. The container of the solution was sealed with a butyl rubber plug and then the solution was maintained at 25° C. On the other hand, P. vulgaris was cultured in 10 ml of a culture medium in an ordinary manner, followed by collecting bacterial cells, washing them with physiological saline and suspending the cells into 1 ml of distilled water. The suspension of bacterial cells was added to the solution of a substrate prepared above with a syringe and the solution was again maintained at 25° C. After 48 hours, magnetically susceptible black precipitates were deposited on the bottom of the container. The resulting precipitates were separated from the bacterial cells by the action of a magnet and then washed with distilled water. The precipitates were examined by X-ray diffraction analysis (see FIG. 7) and were found to be magnetite.

We claim:

1. A method for preparing at least one member selected from the group consisting of iron oxides, iron hydroxides and iron oxyhydroxides comprising: reacting an alkali-producing enzyme with a substrate of the enzyme in a solution containing iron ions to form an alkali substance, thereby alkalanizing the solution by the alkali substance; and obtaining fine particles of the iron compound having an average particle size ranging from about 50 to 500 nm.

2. A method as set forth in claim 1 wherein the alkali-producing enzyme is a hydrolase.

3. A method as set forth in claim 1 wherein the alkali-producing enzyme is an oxidoreductase.

4. A method as set forth in claim 1 wherein the alkali-producing enzyme is urease (EC 3.5.1.5).

5. A method as set forth in claim 1 wherein the alkali-producing enzyme is one prepared, in situ, by bacteria capable of producing an alkali-producing enzyme.

6. A method as set forth in claim 5 wherein the bacteria capable of producing an alkali-producing enzyme is urease-producing bacteria.

7. A method as set forth in claim 1 wherein the solution containing iron ions contains $Fe^{2+}$ as iron ions and the alkalization is carried out in the presence of an oxidizing agent to obtain magnetite and/or iron oxyhydroxides.

8. A method as set forth in claim 7 wherein the iron oxyhydroxides are dehydrated to obtain hematite and/or maghemite.

9. A method as set forth in claim 1 wherein the solution containing iron ions contains $Fe^{2+}$ as iron ions and an oxidizing agent is added to the reaction system after the alkalization to convert whole or part of $Fe^{2+}$ to $Fe^{3+}$ by oxidation to thus obtain magnetite and/or iron oxyhydroxides.

10. A method as set forth in claim 9 wherein the iron oxyhydroxides are dehydrated to obtain hematite and/or maghemite.

11. A method as set forth in claim 1 wherein the solution containing iron ions contains $Fe^{2+}$ and $Fe^{3+}$ as iron ions and molar ratio of $Fe^{2+}$ to $Fe^{3+}$ is adjusted to a range within which magnetite is formed before the completion of the alkalization or before the end of the magnetite formation to obtain magnetite.

12. A method as set forth in claim 11 wherein the molar ratio of $Fe^{2+}$ to $Fe^{3+}$ ($Fe^{2+}:Fe^{3+}$) at which magnetite is formed is in the range of 1:0.5 to 5.

13. A method as set forth in claim 11 wherein the molar ratio of $Fe^{2+}$ to $Fe^{3+}$ ($Fe^{2+}:Fe^{3+}$) at which magnetite is formed is in the range of 1 to 3.

14. A method as set forth in claim 1 wherein the solution containing iron ions contains $Fe^{3+}$ as iron ions to obtain iron hydroxides.

15. A method as set forth in claim 14 wherein the resultant iron hydroxides are reduced to form magnetite.

16. A method as set forth in claim 1 wherein the solution containing iron ions contains $Fe^{3+}$ as iron ions and the alkalization is carried out in the presence of a reducing agent to obtain magnetite.

* * * * *